United States Patent [19]

Haynes et al.

[11] Patent Number: 5,352,576
[45] Date of Patent: Oct. 4, 1994

[54] METHOD OF DETERMINING THE PRESENCE AND TITERS OF ANTI HIV-1 AG27BODIES

[75] Inventors: Barton F. Haynes; Thomas J. Palker, both of Durham

[73] Assignee: Duke University, Durham, N.C.

[21] Appl. No.: 931,416

[22] Filed: Aug. 24, 1992

Related U.S. Application Data

[63] Continuation of Ser. No. 589,591, Sep. 28, 1990, abandoned, which is a continuation of Ser. No. 93,854, Sep. 8, 1987, Pat. No. 5,019,387.

[51] Int. Cl.$^5$ .................. C12Q 1/70; G01N 33/543; G01N 33/536; G01N 33/00
[52] U.S. Cl. .................................. 435/5; 435/974; 436/518; 436/536; 436/86; 436/87; 930/221
[58] Field of Search .................. 435/5, 974; 436/518, 436/536, 86, 87; 930/221

[56] References Cited

U.S. PATENT DOCUMENTS

| | | | |
|---|---|---|---|
| 4,520,113 | 5/1985 | Gallo et al. | 436/504 |
| 4,659,678 | 3/1987 | Forrest et al. | 436/521 |
| 4,725,669 | 2/1988 | Essex et al. | |
| 4,812,556 | 3/1989 | Vahlne et al. | 530/324 |
| 4,956,273 | 9/1990 | Kennedy et al. | |
| 5,013,548 | 5/1991 | Haynes et al. | |
| 5,019,387 | 5/1991 | Haynes et al. | |
| 5,081,226 | 1/1992 | Berzofsky et al. | |

FOREIGN PATENT DOCUMENTS

| | | |
|---|---|---|
| 0255190 | 2/1988 | European Pat. Off. |
| WO02775 | 5/1987 | PCT Int'l Appl. ......... G01N 33/53 |
| 8702775 | 5/1987 | PCT Int'l Appl. |

OTHER PUBLICATIONS

Ratner et al, "Complete Nucleotide Sequence of the AIDS Virus, HTLV-III," Nature, vol. 313, pp. 277-284, 1985.
Palker et al, "A Conserved Region at the COOH Terminus of Human Immunodeficiency Virus gp 120 Envelop Protein Contains an Immunodominant Epitope", Proc. Natl. Acad. Sci. USA. vol. 84, pp. 2479-2483, 1987.
Peter Newmark, "Problems with AIDS Vaccines" Nature, vol. 324, pp. 304–305, 1986.
Colin Norman, "AIDS Virus Presents Moving Target" Science, vol. 230, pp. 1357-1358, 1985.
Takahashi et al J. of Exp. Med. 170: 2023 (1989).
Palker et al. J. of Immunol. 142: 3612 (1989).
Girard et al J. of Cell. Biochem. (Abst. L415) (1990) UCLA Symp on Mol. & Cell Biol. p. 150.
Weinhold et al J. of Cell. Biochem. (Abst. L550) (1990) UCLA Sump on Mol. & Cell. Biol. p. 180.
Palker et al J. Cell. Biochem (Abst. L315) (1990) UCLA Symp on Mol. & Cell Biol. p. 134.
Pert et al; Proc. Natl. Acad. Sci, USA, vol. 83, pp. 9254-9258, Dec. 1986; "Octapeptides Deducted From the Neuropeptide Receptor-Line Pattern of Antigen T4 in Brain Potently Inhibit Human Immunodeficiency Virus Receptor Binding and T-Cell Infectivity".
Sarin et al; Science, vol. 232, pp. 1135-1138, May 30, 1986; "Neutralization of HTLV-III/LAV Replication by Antiserum to Thymosin $\alpha_1$".
Kennedy et al; Science, vol. 231, pp. 1556-1560, Mar. 28, 1986; "Antiserum to a Synthetic Peptide Recognizes the HTVL-III Envelope Glycoprotein".
Chanh et al; The EMBO Journal, vol, 5, No. 11; "Induction of Anti–HIV Neutralizing Antibodies by Synthetic Peptides".
Putney et al; Science, vol. 234, pp. 1392-1395, Dec. 12, 1986; HTLV-III/LAV-Neutralizing Antibodies to an E. Coli-Produced Fragment of the Virus Envelope.

(List continued on next page.)

Primary Examiner—Margaret Parr
Assistant Examiner—Bradley L. Sisson
Attorney, Agent, or Firm—Nixon & Vanderhye

[57] ABSTRACT

Disclosed is a method for determining the presence in mammalian serum of antibodies against specific strains of HIV through the use of SP-10 peptides. The method incorporates the use of SP-10 peptides derived from the following HIV strains: IIIB, MN, RF, SC, WMJ-1, WMJ-2, WMJ-3, ARV-2, and LAV-1.

2 Claims, 7 Drawing Sheets

OTHER PUBLICATIONS

Kennedy et al; The Journal of Biological Chemistry, vol. 262, No. 12, pp. 5769-5774, Apr. 25, 1967; Use of a Resin-Bound Synthetic Peptide for Identifying a Neutralizing Antigenic Determinant Associated With the Human Immunodeficiency Virus Envelope.

Cease et al; Proc. Natl. Acad. Sci USA, vol. 84, pp. 4249-4253, Jun. 1987 Helper T-Cell Antigenic Site Identification in the Acquired Immunodeficiency Syndrome Virus gp 120 Envelope Protein and Induction of Immunity in Mice to the Native Protein Using A 16-Residue Synthetic Peptide.

Ho et al; Journal of Virology, vol. 61, No. 6, pp. 2024-2028, Jun. 1987; Human Immunodeficiency Virus Neutralizing Antibodies Recognize Several Conserved Doamins on the Envelope Glycoproteins.

Krohn et al; Prc. Natl. Acad. Sci. USA, vol. 84, pp. 4994-4998, Jul. 1987 Specific Cellular Immune Response and Neutralizing Antibodies in Goats Immunized with Native or Recombinant Envelope Proteins Derived from Human T-Lymphotropic Virus Type $III_{62}$ and in Human Immunodeficiency Virus-Infected Men.

Starcich et al; Cell, vol. 45, pp. 637-648, Jun. 6, 1986; Identification and Characterization of Conserved and Variable Regions in the Envelope Gene of HTLV-III/LAV, The Retrovirus of AIDS.

Robey et al; Proc. Natl. Acad. Sci. USA, vol. 83, pp. 7023-7027, Sep. 1986; Prospect for Prevention of Human Immunodeficiency Virus Infection: Purified 120-kDa Envelope Glycoprotein Induces Neutralizing Antibody.

Wang et al, Proc. Natl. Acad. Sci. USA vol. 83, pp. 6159-6163, Aug., 1986; Detection of Antibodies to Human T-Lymphotropic Virus Type III by Using a Synthetic Peptide of 21 Amino Acid Residues Corresponding to a Highly Antigenic Segment of gp41 Envelope Protein.

Sodroski et al; Nature, vol. 322, Jul. 31, 1986; Role of the HTLV-III/LAV Envelope in Syncytium Formation and Cytopathicity.

Dalgleish et al; *Nature* "Letters to Nature"; The CD4 (T4) Antigen is an Essential Components of the Receptor for the AIDS Retrovirus (1984).

Hu et al; Nature, vol. 320, Apr. 10, 1986; Expression of AIDS Virus Envelope Gene in Recombinant Vaccinia Viruses.

Chakrabarti et al; Nature, vol. 320, Apr. 10, 1986; Expression of the HTLV-III Envelope Gene by a Recombinant Vaccina Virus.

Zarling et al; The Journal of Immunology, vol. 139, 988-990, Aug. 15, 1987; Proliferative and Cytotoxic T Cells to AIDS Virus Glycoproteins in Chimpanzees Immunized With a Recombinant Vaccinia Virus Expressing AIDS Virus Envelope Glycoproteins.

Hu et al; Nature, vol. 328, Aug. 20, 1987; Effect of Immunization with a Vaccinia-HIV env Recombinant on HIV Infection of Chimpanzees.

Hart et al, "Synthetic Peptides Containing T and B Cell Epitopes From Human Immunodeficiency Virus Envelope gp120 Induce Anti-HIV Proliferative Responses and High Titers of Neutralizing Antibodies in Rhesus Monkeys[1]", The Journal of Immunology, vol. 145, pp. 2677 -2685, No. 8, Oct. 15, 1990.

Hart et al, "HIV Synthetic Peptides Containing T and B Cell Epitopes Induce HIV-Specific CD8+ Cytotoxic T Cell Response *In Vivo*", 1991 FASEB.

LaRosa et al, "Conserved Sequence and Structural Elements in the HIV-1 Principal Neutralizing Determinant", Science, vol. 249 pp. 932-935, Aug. 24, 1990.

Pert et al; Proc. Natl. Acad. Sci., USA, vol. 83, pp. 9254-9258, Dec. 1986; "Octapeptides Deducted from the Neuropeptide Receptor-like Pattern of Antigen T4 in Brain Potently Inhibit Human Immunodeficiency Virus Receptor Binding and T-Cell Infectivity".

Sarin et al; Science, vol. 232, pp. 1135-1138, May 30, 1986; "Neutralization of HTLV-III/LAV Replication by Antiserum to Thymosin $\alpha_1$".

Kennedy et al; Science, vol. 231, pp. 1556-1560, Mar. 28, 1986; "Antiserum to a Synthetic Peptide Recognizes the HTLV-III Envelope Glycoprotein".

Chanh et al; The EMBO Journal, vol. 5, No. 11; Induction of Anti-HIV Neutralizing Antibodies by Synthetic Peptides".

Putney et al; Science, vol. 234, pp. 1392-1395, Dec. 12, 1986; "HTLV-III/LAV-Neutralizing Antibodies to an *E. Coli*-Produced Fragment of the Virus Envelope".

Kennedy et al; The Journal of Biological Chemistry, vol. 262, No. 12, pp. 5769-5774, Apr. 25, 1967; "Use of (List continued on next page.)

OTHER PUBLICATIONS

Resin–Bound Synthetic Peptide for Identifying a Neutralizing Antigenic Determinant with the Human Immunodeficiency Virus Envelope".

Javaherian et al, "Principal neutralizing domain of the human immunodeficiency virus type 1 envelope protein", Proc. Natl. Acad. Sci. USA, vol. 86, pp. 6768–6772, Sep. 1989.

Takahashi et al, "Structural Requirements for Class I MHC Molecule–Cytotoxic T Cell Recognition of an Immunodominant of the Human Immunodeficiency Virus Envelope Protein", J. of Exp. Med. 170:02023 (1989).

Palker et al, "Polyvalent Human Immunodeficiency Virus Synthetic Immunogen Comprised of Envelope gp 120 T Helper Cell Sites and B Cell Neutralization Epitopes", J. of Immunol. 141:3612 (1989).

Girard et al, J. of Cell. Biochem. (Abst. L415) (1990) UCLA Sump. on Mol. and Cell Biol., p. 150.

Weinhold et al. J. Cell. Biochem. (Abst. L550) (1990) UCLA Symp. on Mol. and Cell. Biol., p. 180.

Palker et al. J. Cell. Biochem. (Abst. L315) (1990) UCLA Symp. on Mol. and Cell Biol., p. 134.

Palker et al, "Type-specific neutralization of the human immnodeficiency virus with antibodies to env–encoded synthetic peptides", Proc. Natl. Acad. Sci. USA, vol. 85, pp. 1932–1936, Mar. 1988.

Letter to the Editor, "Detection of a Fusion Peptide Sequence in the Transmembrane Protein of Human Immunodeficiency Virus", Cell, vol. 50, pp. 327–328, Jul. 31, 1987.

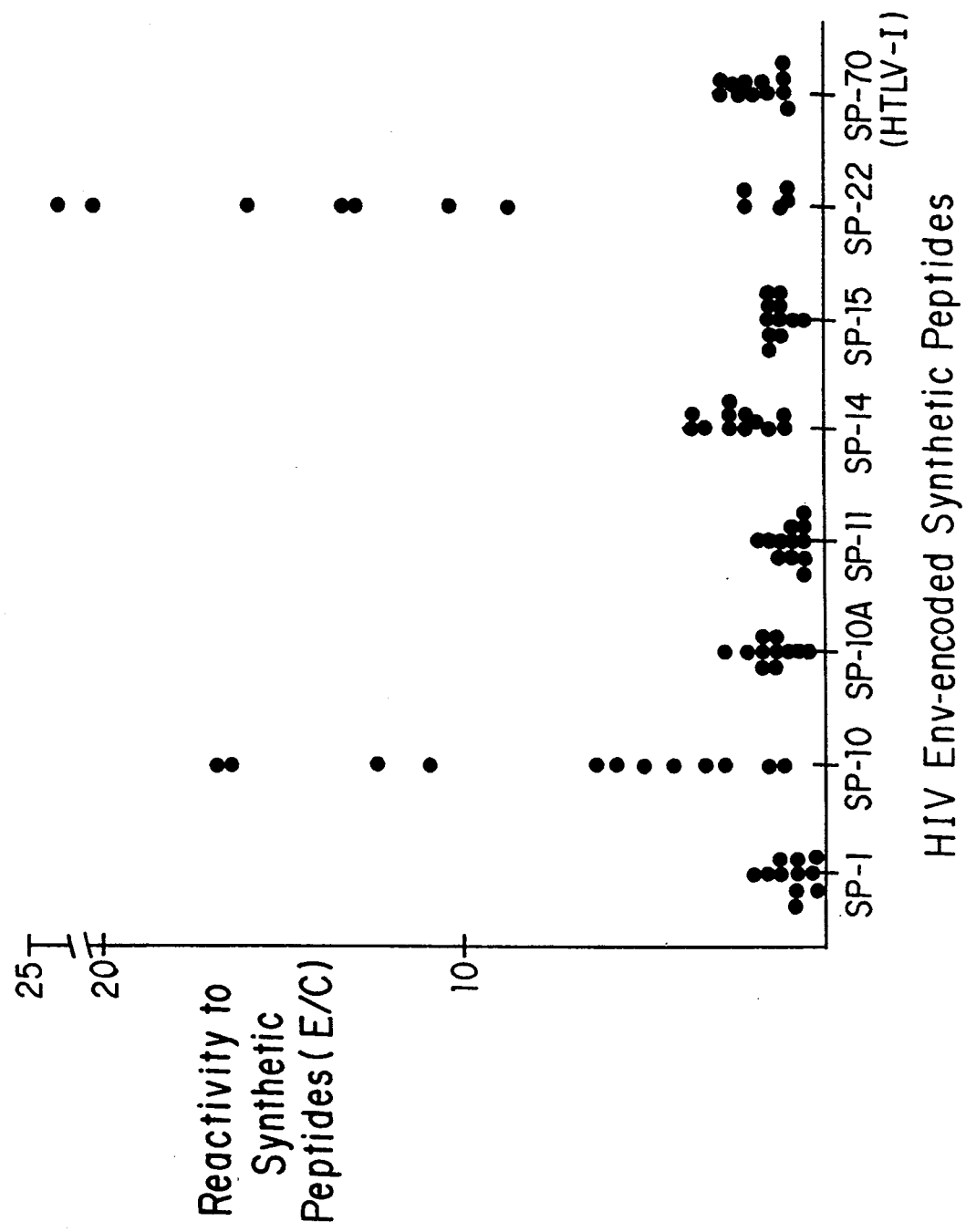

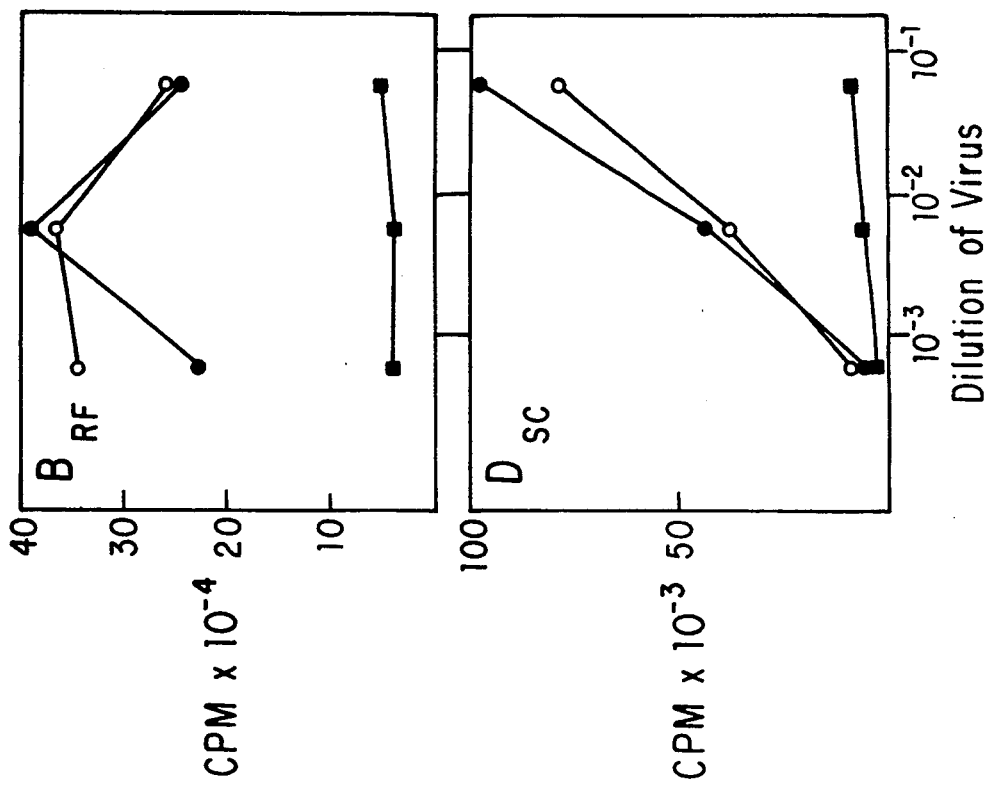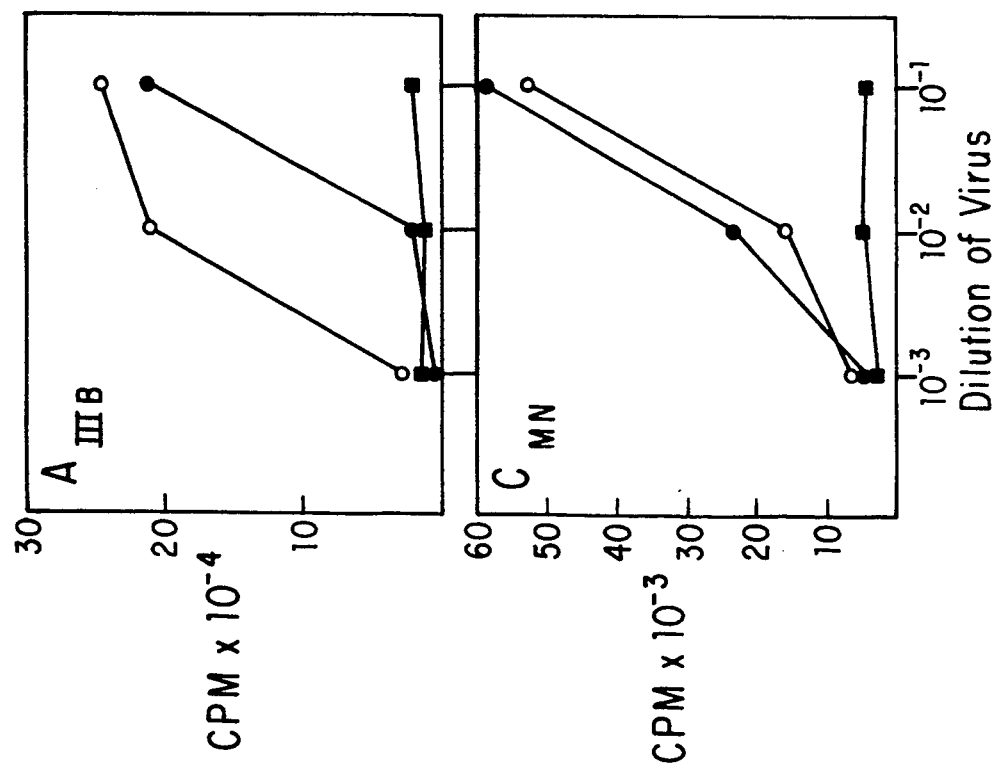

METHOD OF DETERMINING THE PRESENCE AND TITERS OF ANTI HIV-1 AG27BODIES

This is a continuation of application Ser. No. 07/589,591, filed on Sep. 28, 1990, which was abandoned upon the filing hereof, which is a continuation of application Ser. No. 07/093,854, filed Sep. 8, 1987, U.S. Pat. No. 5,019,387.

BACKGROUND OF THE INVENTION

Technical Field

The present invention relates to peptides comprising amino acid sequences corresponding to a region of the human immunodeficiency virus (HIV) envelope protein, and to methods of determining the presence and titers of anti-HIV-1 antibodies using same.

Background Information

The human retrovirus HIV has been demonstrated to be the causative agent of acquired immunodeficiency syndrome (AIDS), a disease for which there is currently no cure. The epidemiologic pattern among AIDS-related cases indicates that it is a transmissible disease. The virus is frequently found in saliva, semen, whole blood and plasma from individuals in high risk categories, including male homosexuals, intravenous drug users, patients receiving blood products, and individuals from Haiti and Central Africa. The rapid rise in seropositivity among individuals in high risk categories, the virulence of the disease, and its growing world-wide distribution, underscore an overwhelming and immediate need for a vaccine capable of inducing complete protective immunity in non-infected individuals. The need for diagnostic reagents to be used in testing for the presence of antibodies against HIV in biological samples is also clear.

Previous work has demonstrated that HIV infects T lymphocytes of the immune system by attaching its external envelope glycoprotein (gp120) to the CD4 (T4) molecule on the surface of T lymphocytes, thus using the CD4 (T4) molecule as a receptor to enter and infect T cells. After infecting the cell, the virus subverts the ability of the T cell to fend off the virus.

Retroviral envelope glycoproteins have been shown to be important in evoking a virus-neutralizing antibody response, as determined by the ability of sera containing anti-envelope antibodies to inhibit HIV infection in vitro. Specifically, the HIV external envelope glycoprotein gp120 has been shown to be capable of inducing neutralizing antibodies in goats and in man (Robey et al., *Proc. Nat'l. Acad. Sci. (USA)* 83: 7023, 1986). Little is known of the precise location of epitopes on gp120 that are either immunogenic in HIV-infected patients or that give rise to neutralizing antibodies. However, the recombinant protein PB1 (Putney et al., *Science*, 234:1392, 1986), which encodes approximately one-third of the entire gp120 molecule, has been shown to include the part of the envelope protein that induces the formation of neutralizing antibodies.

The data accumulated to date suggest that neither PB1 nor intact gp120 are appropriate for use in a vaccine against HIV infection. Studies involving the use of goats and chimpanzees demonstrate that neither molecule has the ability to induce the production of high titers of neutralizing antibodies. In addition, it has been shown that the intact gp120 molecule binds to the T4 molecule of normal T cells and is capable of disrupting normal immune function. Specifically, whole gp120 envelope molecules interfere with normal CD4 (T4) function and suppress T cell activation in vitro (Mann et al., *J. Immunol.* 138:2640, 1987). Thus, the administration of vaccines comprising large pieces of the external envelope glycoprotein may actually be detrimental to the normal immune system.

Thus, critical to the development of a vaccine against HIV, is the generation of an antibody response against gp120 that will interfere with gp120 interaction with the CD4 (T4) molecule, but will not interfere with normal CD4 (T4) interaction with class II major histocapatibility molecules, a major normal function of the CD4 (T4) molecule in the mediation of a myriad of stages of normal T cell responses. In addition, an effective vaccine against HIV will induce protective immune responses in primates and in man, that is, will prevent subsequent HIV infection from occurring.

OBJECTS OF THE INVENTION

It is an object of the present invention to provide a peptide that, when linked to a carrier molecule and/or polymerized to form molecular aggregates, is capable of inducing the production in mammals of high titers of neutralizing antibodies against HIV, which peptide does not disturb normal immune function.

It is an additional object of the invention to provide a method of detecting the presence of anti-gp120 antibodies in biological test samples.

SUMMARY OF THE INVENTION

The invention relates to immunogenic preparations. Peptides having amino acid sequences corresponding to antigenic determinants of the envelope protein of HIV are covalently coupled, either directly or through spacer molecules, to suitable carrier molecules.

In one embodiment, the present invention comprises an essentially pure form of a peptide having an amino acid sequence corresponding to an antigenic determinant of the envelope glycoprotein of HIV, which peptide is capable, when covalently linked to a carrier molecule, of inducing in a mammal high titers of protective antibodies against HIV. The peptide can have, for example, the sequence CTRPNNNTRKSIRIQRGPG, corresponding to amino acids 303–321 of the envelope glycoprotein of the HTLV-III$_B$ isolate (Rather et al., *Nature* 313:277, 1985), or any portion thereof.

In another embodiment, the present invention comprises an immunogenic conjugate capable of inducing in a mammal high titers of protective antibodies against HIV, said conjugate comprising: (i) a carrier molecule covalently attached to (ii) a peptide comprising an amino acid sequence corresponding to an antigenic determinant of the envelope glycoprotein of HIV.

In yet another embodiment, the present invention comprises a method of producing immunity to HIV comprising administering the above-described conjugate to a mammal.

In another embodiment, the present invention comprises a method of detecting the presence of anti-gp120 antibodies in biological test samples.

BRIEF DESCRIPTION OF THE DRAWINGS

FIG. 2. Reactivity of AIDS patient antibodies to synthetic peptides.

FIG. 3. Reactivity to gp120 of antibodies from HIV+ patient purified over synthetic peptide affinity columns.

FIG. 5. Isolate specific neutralization of HIV. Ability of ● goat anti-SP-10 antiserum, ▲ pre-immune goat serum and (○) AIDS patient serum to neutralize four different HIV isolates (FIG. 5A) HTLV-III$_B$ (FIG. 5B) HTLV-III$_{RF}$ (FIG. 5C) HTLV-III$_{MN}$ (FIG. 5D) HTLV-III$_{SC}$.

DETAILED DESCRIPTION OF THE INVENTION

Figure 1:
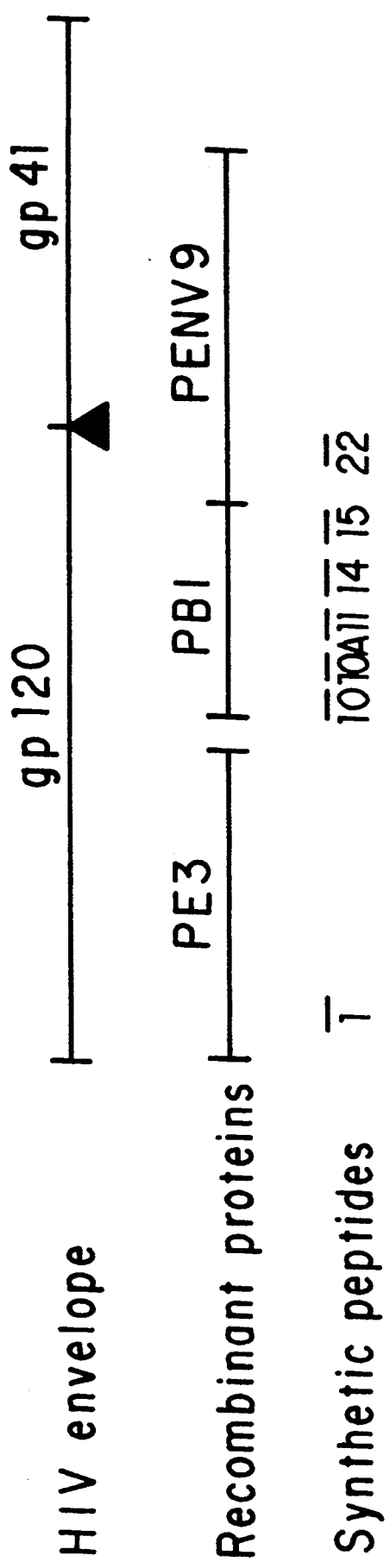
FIG. 1. Recombinant proteins and relation to synthetic peptides.

The present invention relates to peptides corresponding to immunogenic epitopes of HIV. These novel immunogenic agents are prepared by chemically synthesizing peptides sharing antigenic determinants with the envelope protein of HIV. The peptides are linked to carrier molecules (and/or are polymerized).

It was determined that peptides that should be studied for immunogenic potential included those corresponding to hydrophilic, charged regions of the HIV envelope glycoprotein. It was further determined that, of such peptides, those with predicted beta turns would likely be of particular importance. It was recognized that the formation of intrapeptide disulfide bonds would be useful in establishing native configurational determinants. Also, it was recognized that formation of interchain disulfide bonds would be useful in polymerizing peptide molecules so as to form larger, more immunogenic peptide aggregates.

Computer analysis of the predicted amino acid sequence of the envelope protein of the HTLV-III$_B$ and ARV-2 isolates of HIV established the secondary structure and location of hydrophilic regions. Secondary structure was determined from the computer analysis using the method of Chou and Fasman (*Biochemistry* 13:211 and 13:222, 1974; *Advances in Enzymology* 47:45, 1978). Potential areas of beta turns were localized using the method of Rose (*Nature* 272:586, 1978). Hydrophilic regions of the envelope protein were identified by the technique of Rose and Roy (*Proc. Nat'l. Acad. Sci. USA* 77:4643, 1980).

The peptides of the instant invention correspond to, or are homologous with, B-cell epitopes present within the central region of the HIV isolate HTLV-III$_B$ envelope protein, or envelope protein of related HIV isolates. The peptides of the present invention are about 35 amino acids (units) or less in length, are hydrophilic, and when conjugated to appropriate carrier molecules, evoke the production in mammals of high titers (that is, advantageously, a reduction in infectivity of 100 infectious units of approximately 80% in vitro at 1:600 dilution of serum) of type (or isolate) specific neutralizing antibodies against HIV. Unlike the intact gp120 molecule, the peptides themselves are not capable of inhibiting interaction between the CD4 (T4) molecule on the surface of T lymphocytes and macrophage HLA class II molecules, and thus do not interfere with normal immune function. That is, peptides of the instant invention capable of inducing anti-HIV neutralizing antibodies, do not inhibit antigen-specific normal T cell proliferative responses in vitro.

Peptides of the instant invention can have, for example, the sequence CTRPNNNTRKSIRIQRGPG (designated SP-10), corresponding to amino acids 303–321 of the HTLV-III$_B$ envelope glycoprotein gp120 (Ratner et al., *Nature* 313:277, 1985), or some portion of that sequence. Peptides of the invention can also have sequences corresponding to the analogous SP-10 regions of HIV isolates other than HTLV-III$_B$, or portions thereof, these sequences being designated "SP-10-like" (see, for example, sequences in Table I).

TABLE I

| SP-10 and SP10-Like Sequences | |
|---|---|
| SP-10 III$_B$ | CTRPNNNTRKSIRIQRGPG |
| SP-10 MN | CTRPNYNKRKRIHIGPGRAF |
| SP-10 RF | CTRPNNNTRKSITKGPGRVIY |
| SP-10 SC | CTRPNNNTTRSIHIGPGRAFY |
| SP-10 WMJ-1 | CTRPNNNVRRRHIHIGPGRAFY |
| SP-10 WMJ-2 | CTRPYNNVRRSLSIGPGRAFR |
| SP-10 WMJ-3 | CTRPNDIARRRIHIGPGRAFY |
| SP-10 ARV-2 | CTRPNNNTRKSIYIGPGRAFH |
| SP-10 LAV-I | CTRPNNNTRKSIRIQRGPG |
| SP-10 HIV-2 (LAV-2) | CKRPGNKTVKQIMLMSGHVFHSHY |

The expression "SP-10-like" includes within its meaning the SP-10 sequence itself.

Carrier molecules to which peptides of the invention are covalently linked (conjugated) are advantageously, non-toxic, pharmaceutically acceptable and of a size sufficient to produce an immune response in mammals. Examples of suitable carrier molecules include tetanus toxoid, keyhole limpet hemocyanin (KLH), and peptides corresponding to T cell epitopes (that is, T1 and T2) of the gp120 envelope glycoprotein that can substitute for non-AIDS virus-derived carrier molecules (Cease, *Proc. Nat'l. Acad. Sci.* (*USA*) 84:4249, 1987; Kennedy et al., *J. Biol. Chem.* 262:5769, 1987). Peptides can also be administered with a pharmaceutically acceptable adjuvant, for example, alum, or conjugated to other carrier molecules more immunogenic than tetanus toxoid.

Linkage of a carrier molecule to a peptide of the invention can be direct or through a spacer molecule. Spacer molecules are, advantageously, non-toxic and reactive. Two glycine residues added to the amino terminal end of the peptide can provide a suitable spacer molecule for linking SP-10-like sequences, or portions thereof, to a carrier molecule; alternatively, SP-10-like sequences, or portions thereof, can for example be synthesized directly adjacent to, for example, another immunogenic HIV envelope sequence, for example, T1 or T2. Cysteines can be added either at the N or C terminus of the SP-10-like peptide for conjugation to the carrier molecule or to both ends to facilitate interchain polymerization via di-sulfide bond formation to form larger molecular aggregates.

Conjugation of the carrier molecule to the peptide is accomplished using a coupling agent. Advantageously, the heterofunctional coupling agent M-maleimidobenzoyl-N-hydroxysuccinimide ester (MBS) or the water soluble compound m-maleimido-benzoylsulfosuccinimide ester (sulfo-MBS) is used, as described by Green et al (Cell, 28:477; 1982) and by Palker et al. (*Proc. Nat'l Acad. Sci.* (*U.S.A.*) 84:2479, 1987).

Advantageously, the SP-10 sequence of HTLV-III$_B$ (see Table I) can be conjugated to or synthesized with either the HTLV-III$_B$ gp120 envelope T cell epitope T1 (amino acids 428–443 of gp120), KQIINMWQEVG-KAMYA, or to the T2 epitope (amino acids 112–124 of HTLV-III$_B$ gp120), HEDIISLWNQSLK (Cease et al., *Proc. Nat'l. Acad. Sci* (*USA*) 84:4249, 1987) to form a single polypeptide (in the case of T1-SP-10 from the HTLV-III$_B$ isolate of HIV, KQIINMWQEVG-KAMYACTRPNNNTRKSIRIQRGPG). Similarly, T1 or T2 sequences from other HIV isolates can be linked to synthetic peptides derived from the SP-10 region of the corresponding isolates (see Table I), advantageously, at the N terminus of the SP-10-like peptide, to make a T1(or T2-)-SP-10-like peptide capable of inducing neutralizing antibody titers against a specific strain of HIV. Linkage at the C terminus of the SP-10-like peptide is also possible.

Smaller portions of SP-10-like peptides, for example, SP-10 RF(A) and SP-10 C (Table II) can also be covalently linked to carrier molecules, including gp120 T cell epitopes, and used in a vaccine. There is a major hypervariable region that is carboxy terminal to peptides designated as SP-10-like in Table I (envelope amino acids 322–333, Ratner et al, *Nature* 313:277, 1985), and the hypervariable region may play a role in enhancing the ability of SP-10-like peptides to raise type-specific neutralizing antibodies. Thus, amino acid sequences corresponding to a hypervariable region (approximately amino acids 322–333) of HIV isolates can be used, in part or in whole, as described for other SP-10-like peptides (see, for example, sequences in Table II). Hypervariable sequences are linked advantageously C-terminal to the SP-10-like peptide. Linkage N-terminal to the SP-10-like peptide is also possible.

SP-10-like-hypervariable region-cysteine polypeptides. The polypeptides can be treated with oxidizing agents to induce disulfide bonds between polypeptide chain cysteines, to effect polymerized and therefore, highly immunogenic antigens. The molecular aggregates thus formed advantageously comprise SP-10-like peptides derived from (corresponding to) at least 2 HIV isolates.

The instant invention relates, advantageously, two or more conjugates comprising an SP-10-like sequence, or portion thereof (see, for example, sequences in Table 1) derived from 2 or more HIV isolates, and a carrier molecule such as tetanus toxoid, or two or more T1- or T2-SP-10-like peptide conjugates, wherein both the T1 (or T2) and the SP-10-like sequences correspond to sequences present in a specific HIV isolate.

The advantage of using, as a carrier molecule, a synthetic peptide reflecting a portion of the gp120 molecule recognized by helper T cells, is that no other carrier molecule, such as tetanus toxoid, would be required, and the B and T cell response to HIV would be specific. Combining several peptides reflecting sequences from the SP-10 region of different isolates, and possibly the T cell recognition region of the gp120 envelope, overcomes the problem of isolate-specific neutralization.

The present invention also relates to SP-10-like peptides linked to hypervariable sequences described above (see, for example, Table II). A mixture of such polypeptides, coupled to appropriate carrier molecules and/or polymerized via disulfide bond formation (Harington, C. R., et al., *Biochem. J.*, 30:1598, 1930; Harington, C. R., et al., *Biochem. J.*, 38;417, 1944; Weygand et al., *Z. Naturforsch.*, 176:807, 1962), can be used to evoke a protective antibody response to multiple isolates of HIV.

SP-10-like peptides can be used in a solid phase radioimmunoassay (Palker et al. *J. Immunol* 136:2393, 1986; ibid., *Proc. Nat'l. Acad. Sci.* (*USA*) 84:2479, 1987) to (i) detect the presence and titers of neutralizing antibodies of HIV; and (ii) to determine with which strain of HIV the patient is infected. Thus, in addition to SP-10-like peptides being used as a vaccine or a component of a

TABLE II

| SP-10 and SP-10-like sequences containing an additional carboxyterminal hypervariable domain and shortened SP-10-like sequences. | |
|---|---|
| SP-10 IIIB | CTRPNNNTRKSIRIQRGPGRAFVTIGKIGN |
| SP-10 MN | CTRPNYNKRKRIHIGPGRAFYTTKNIIGT |
| SP-10 RF | CTRPNNNTRKSITKGPGRVIYATGQIIGD |
| SP-10 SC | CTRPNNNTTRSIHIGPGRAFYATGDIIGD |
| SP-10 WMJ-1 | CTRPNNNVRRRHIHIGPGRAFYTGEIRGN |
| SP-10 WMJ-2 | CTRPYNNVRRSLSIGPGRAFRTREIIGI |
| SP-10 WMJ-3 | CTRPNDIARRRIHIGPGRAFYTGKIIGN |
| SP-10 ARV-2 | CTRPNNNTRKSIYIGPGRAFHTTGRIIGD |
| SP-10 LAV-I | CTRPNNNTRKSIRIQRGPGRAFVTIGKIGN |
| SP-10 HIV-2 (LAV-2) | CKRPGNKTVKQIMLMSGHVFHSHYQPINKRPRQ |
| SP-10 C | CTRKSIRIQRGPGR(Y) |
| SP-10 RF(A) | CRKSITKGPGRVIY |

The present invention also relates to a combination of a SP-10-like sequence and a carrier molecule, and a peptide corresponding to the HIV gp41 transmembrane region that is involved in viral-induced cell fusion, FLGFLG, (Gallagher, *Cell* 50:327, 1987). The FLGFLG sequence is added, advantageously, at the C terminus of the SP-10-like peptide. Addition at the N terminus of the SP-10-like peptide is also possible.

The present invention also relates to cysteine-T1-(or T2-)SP-10-like, cysteine-T1-(or T2-)SP-10-like-hypervariable region, or cysteine-T1-(or T2-) SP-10-like-FLGFLG polypeptides; and/or SP-10-like-cysteine or vaccine, the peptide can be used, as described above, for diagnostic purposes. Peptides of the instant invention can also be used in standard enzyme linked immunosorbent assays to detect the presence of HIV antibodies.

The following nonlimiting examples illustrate the invention in more detail.

EXAMPLE 1

Synthesis of Peptides and Preparation of Conjugates

Synthetic essentially pure peptides containing hydrophilic amino acid sequences from the HTLV-III$_B$ envelope glycoprotein gp120 (Ratner, et al. *Nature*, 313:277, 1985) were synthesized on an Applied Biosystems 430A peptide synthesizer using chemical and program cycles supplied by the manufacturer. Sequences of synthetic peptides are given in Table III.

TABLE III

SYNTHETIC PEPTIDES WITH HYDROPHILIC AMINO ACID SEQUENCES OF HTLV-III$_B$ ENVELOPE PROTEIN

| Synthetic Peptide | Amino Acid Number[a] | Sequence[b] |
|---|---|---|
| SP-1 | 80–91 | ACVPTDPNPQEV(Y) |
| 10 | 303–321 | CTRPNNNTRKSIRIQRGPG(Y) |
| 10A | 328–344 | (Y)GKIGNMRQAHCNISRAK |
| 11 | 341–363 | (Y)SRAKWNNTLKQIDSKLREQFGNN(C) |
| 14 | 393–421 | (Y)NSTQLFNSTWFNSTWSTKGSNNTEGSDTI(C) |
| 15 | 461–475 | (Y)LTRDGGNSNNESEIF(C) |
| 22 | 504–518 | APTKAKRRVVQREKR(C) |

[a] According to Ratner et. al., *Nature*, 313:277, 1985.
[b] Amino acids in parentheses were added for iodination of peptide (Y) and coupling to carrier protein (C).

The relationship of the peptides synthesized to known recombinant proteins PE3, PBI and PENV9 is shown in FIG. 1 (Putney et al., *Science*, 234:1392, 1986; Petteway et al., *Viruses and Human Cancer: UCLA Symposia on Molecular and Cellular Biology* 1987).

Peptides were conjugated to carrier molecules such as bovine serum albumin (BSA) or tetanus toxoid (TT) with MBS, as described by Green et al. (*Cell*, 28:477, 1982; Palker et al, *Proc. Natl. Acad. Sci.* (*USA*) 84:2479, 1987). For the coupling procedure, 24 mg of tetanus toxoid (for example) in 0.5 ml of phosphate buffered saline, pH 7.2, was incubated with 1 mg of MBS dissolved in 100 μl of dimethylformamide for 1 hr. at 23° C. Tetanus toxoid treated with MBS (TT-MBS) was then subjected to sieving chromatography on a PD-10 (Pharmacia) column to remove unreacted MBS from TT-MBS, and fractions containing TT-MBS were recovered in the void volume of the column as determined by spectrophotometric assay at an optical density of 280 nm. TT-MBS was then incubated with rocking at 23° C. for 3 hr. with 6–9 mg of synthetic peptide (molar ratio 30:1, peptide carrier protein) in PBS containing reduced cysteine at either the carboxyl or amino terminus. TT-peptide conjugates were dialyzed overnight at 4° C. against PBS or again desalted on a PD-10 column and were used as an immunogen.

Conjugation of peptides to BSA or tetanus toxoid was monitored by subjecting conjugates to sodium dodecylsulfate-polyacrylamide gel electrophoresis (SDS-PAGE) under non-reducing conditions and by measuring the increase in apparent molecular weights over that of BSA and TT treated with MBS. Coupling efficiencies also monitored by trace iodination of peptides varied from 10–30% depending on the peptide.

EXAMPLE 2

Reactivity of AIDS Patient Antibodies To Synthetic Peptides

Synthetic peptides derived from hydrophilic regions of gp120 coupled to BSA were used as antigens in a radioimmunoassay (RIA) with HIV+ patient sera (N=12) and normal serum control (N=4), to evaluate the AIDS patient antibody response to epitopes on gp120 (FIG. 2) (Palker et al., *J. Immunol.* 136:2393, 1986; ibid, *Proc. Nat'l. Acad. Sci* (*USA*), 84:2479, 1987). The majority of HIV+ patient sera reacted with two synthetic peptides, SP-10 (9/12, 75%) and SP-22 (8/12, 67%).

Results are expressed as a ratio (E/C) of duplicate cpm values obtained with experimental (E) AIDS sera and control (C) serum samples. E/C>3.0=positive.

EXAMPLE 3

Figure 3A:
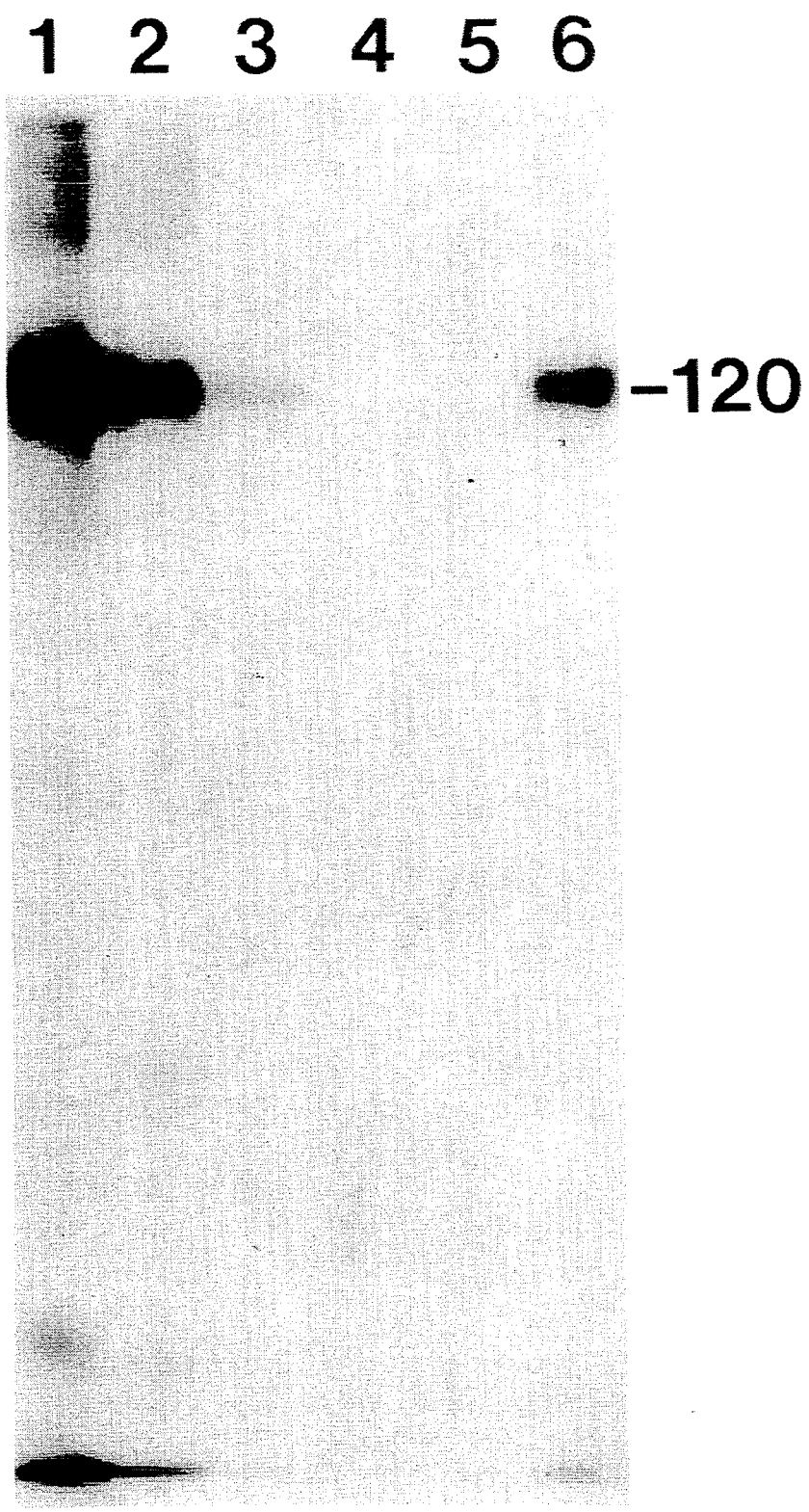
(FIG. 3A) RIP assay of bound antibodies from the SP-10 (lane 1), SP-10A (lane 2), SP-11 (lane 3), SP-14 (lane 4), SP-15 (lane 5) and SP-22 (lane 6) affinity columns tested with gp120-III$_B$.
Figure 3B:
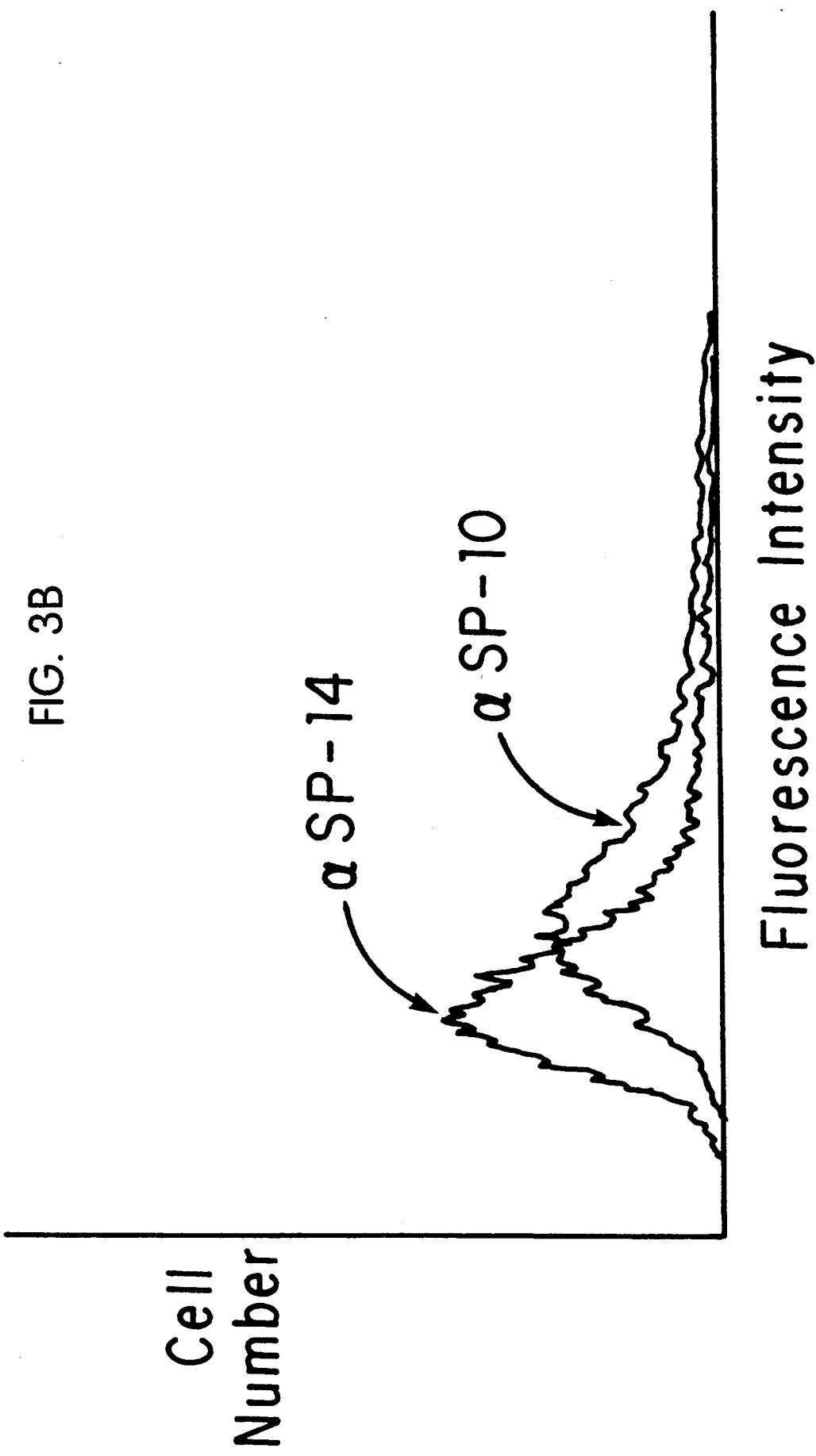
(FIG. 3B) Reactivity to the surface of H-9 cells infected with HTLV-III$_B$ in indirect immunofluorescence assays.

Reactivity of gp120 to Antibodies from HIV+ Patient Purified Over Synthetic Peptide Affinity Columns For preparation of affinity columns, synthetic peptides containing amino acid sequences from HTLV-III$_B$ gp120 (SP-10, 10A, 11, 14, 15, 22, see FIG. 1) were coupled to BSA and then covalently linked to CNBr-activated Sepharose. Serum aliquots (2 ml) from an HIV seropositive patient were then passed over each column and the antibodies that bound to the affinity columns were then tested for reactivity to purified $^{125}$-labelled HTLV-III$_B$ gp120 in RIP assay (FIG. 3A) and for reactivity to the surface of H-9 cells infected with HTLV-III$_3$ in indirect immunofluorescence assays (FIG. 3B).

A) In RIP assay (Palker et al., *Proc. Nat'l. Acad. Sci* (*USA*) 84:2479, 1987; ibid, *J. Immunol.* 136:2393, 1986), bound antibodies from the SP-10 (lane 1), SP-10A (lane 2), SP-11 (lane 3), and SP-22 (lane 6) affinity columns reacted with gp120-III$_B$ in RIP assay, with antibodies from the SP-10 column showing the greatest reactivity to gp120-III$_B$.

B) When tested in FACS analysis (Shapiro, *Practiced Flow Cytometry*, Alan R. Liss Pub., NY, NY, 1985), antibodies reactive with synthetic peptide SP-10 bound to the surface of HIV-infected cells while binding of affinity purified antibodies to SP-14 or to SP-10A, 11, 15 or 22 (not shown) was not detected. These data suggest that the antigenic site(s) defined by SP-10 are accessible to antibody binding when gp120 is present on the surface of HIV+cells.

EXAMPLE 4

Neutralization of HIV by Goat Anti-SP-10 Antisera

Figure 4:
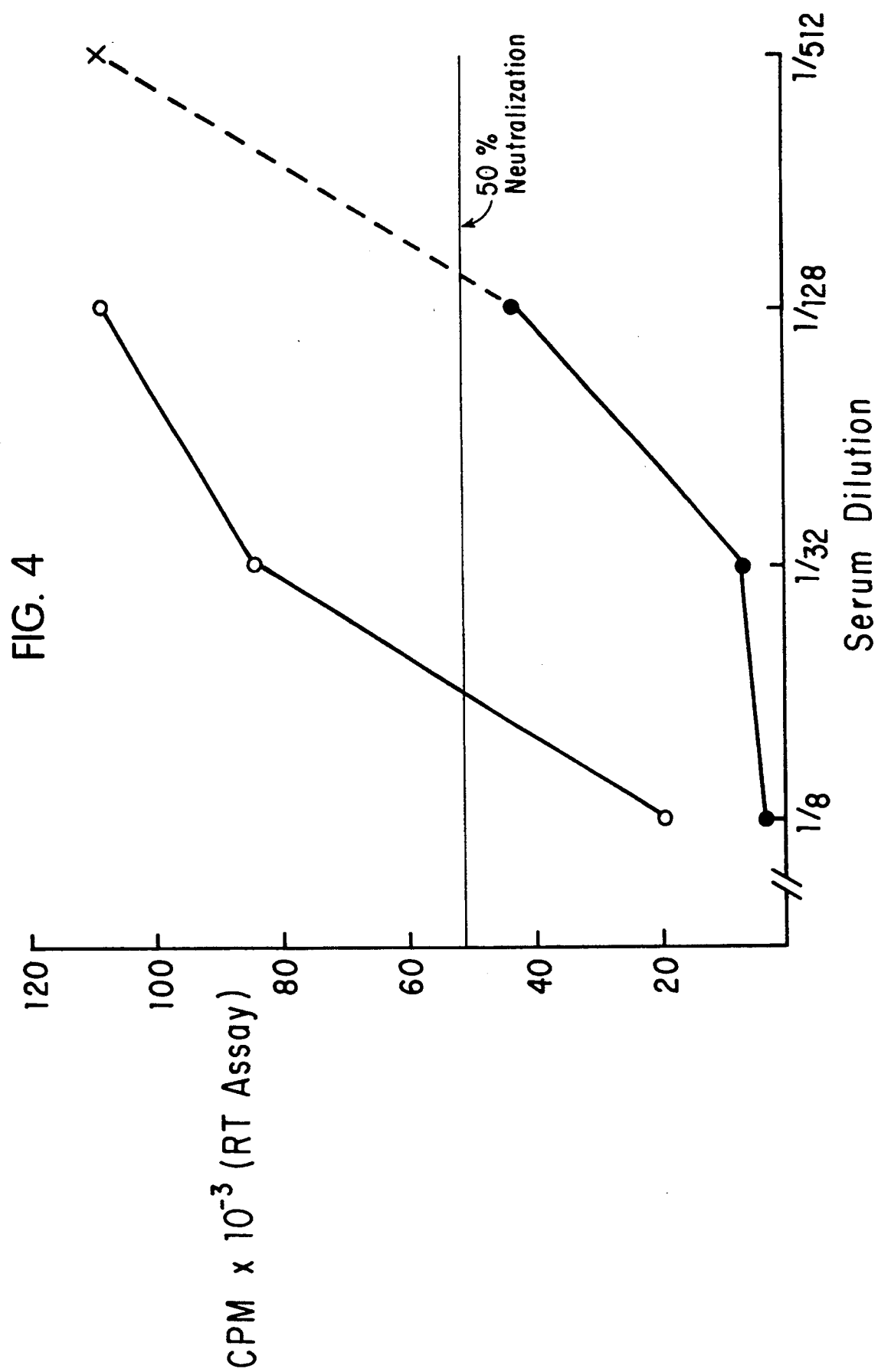
FIG. 4. Neutralization of HTLV-III$_B$ by goat anti-SP-10 antisera.

Goats were immunized subcutaneously with 28 mg of tetanus toxoid SP-10 conjugates (SP-10-TT) in Freunds complete adjuvant (days 0) followed by biweekly inoculations in incomplete Freunds adjuvant (days 14 and 28). Serum samples were collected after the second immunization and tested for the ability to inhibit (i.e. neutralize) HIV infection of H-9 T cells in vitro as measured by the presence of reverse transcriptase (RT) activity in cell culture supernatants (FIG. 4). Decreased cpm values obtained in RT assays reflect decreased levels of HIV after cocultivation of virus and cells for 10 days.

When pre-incubated with 100 infectious units of HTLV-III$_B$, goat anti-SP-10 antiserum neutralized the ability of HIV isolate HTLV-III$_B$ to infect H-9 T cells (●-◆, 50% neutralization titer=1/145). In contrast, serum collected from the same goat prior to immunization did not appreciably neutralize HTLV-III$_B$ (O—O, 50% neutralization titer=1/16).

The original animal injected with SP-10-TT (whose serum neutralized HTLV-III$_B$ in reverse transcriptase assay) was subsequently injected with additional doses of SP-10-TT (0.5 mg/kg body weight). The 50% neutralization titer rose to 1:1600 after two injections. Neutralization data from these and other experiments with SP-10-like peptides are shown in Table IV as the serum dilutions that result in 80% rather than 50% neutralizations of HIV.

In addition, a second goat was injected twice with 0.5 mg/kg doses of SP-10-TT. Serum from the second goat neutralized HTLV-III$_B$ at a titer of 1:100. Importantly, both sera raised in goats also inhibited HTLV-III$_B$ infectivity of T cells in the syncytium-inhibition assay (Table IV).

The syncytium-inhibition assay (Lifson et al., Nature 323:725, 1986) measures the ability of antibodies to inhibit the fusion of HIV-infected T cells, those expressing HIV gp120 envelope protein on the cell surface, with CD4 (T4)+ uninfected T cells. The CD4 (T4) molecule serves as the receptor for the AIDS virus (Maddon et al., Cell 47:333, 1986). The result of fusion of these two cell types is the formation of giant cells that are infected with HIV. In many instances, the result of HIV infection of cells and giant cell formation is death of the infected cell (Zagary et al., Science 231:850, 1986).

of blocking the binding of HIV gp120 protein to T cell CD4 (T4) molecules. In addition, goat antiserum raised to a peptide [SP-10 RF(A)] containing SP-10-like sequence from HIV isolate HTLV-III$_{RF}$ inhibited syncytium formation by HTLV-III$_{RF}$ but not by HTLV-III$_B$.

EXAMPLE 5

Induction of Antibodies Capable of Inhibiting HIV gp120-CD4 (T4) Interactions

A series of studies were undertaken to determine 1) whether the SP-10 peptide conjugated either to bovine albumin or to tetanus toxoid, exerted any inhibitory effect on antigen-specific, CD4 (T4) dependent, T cell responses in vitro; and 2) whether the anti-SP-10 antiserum (described in Example 4) bound to human white blood cell populations not infected with HIV.

When the SP-10 peptide was added directly in vitro human uninfected peripheral blood lymphocyte cultures stimulated with tetanus toxoid, no inhibition of normal T cell response to tetanus toxoid was observed (Table V).

TABLE V

SP-10-TT and SP-10-BSA DO NOT INHIBIT ANTIGEN SPECIFIC PROLIFERATIVE RESPONSES OF NORMAL HUMAN PERIPHERAL BLOOD LYMPHOCYTES

| Additive to Normal Human Peripheral Blood Lymphocytes in Culture | Exp. No. 1 CPM × 10$^6$ Lymphocytes | Exp. No. 2 |
|---|---|---|
| Media Alone | 3,900 | 3,100 |
| TT Alone (1:32) | 175,000 | 61,000 |
| SP-10-TT Alone (1 mg/ml) | 285,500 | 100,400 |
| SP-10-TT (1 mg/ml) + TT (1:32) | 269,500 | 94,400 |
| SP-10-BSA Alone (1 mg/ml) | 8,500 | 35,800 |
| SP-10-BSA (1 mg/ml) + | 262,900 | 144,200 |

TABLE IV

EFFECT OF ANTI-SP-10 ANTISERA ON INFECTIVITY OF HIV ISOLATES HTLV-III$_B$, HTLV-III$_{RF}$, AND HTLV-III$_{MN}$

| Goat # | Inoculum[1] | # of Immunizations | Days Post Immunization | Syncytium Inhibition[2] Using HIV Isolates | | Neutralization of[3] HIV Isolates | | |
|---|---|---|---|---|---|---|---|---|
| | | | | III$_B$ | III$_{RF}$ | III$_B$ | III$_{RF}$ | III$_{MN}$ |
| 70 | SP-10 IIIB-TT | 0 | 0 | — | — | <10 | <10 | <10 |
| | | 2 | 29 | — | — | 50 | <10 | <10 |
| | | 3 | 72 | +(40) | — | 600 | <10 | <10 |
| | | 4 | 96 | +(>80) | — | 250 | <10 | <10 |
| | | 5 | 112 | +(>80) | — | ND | ND | ND |
| 86 | SP-10 IIIB-TT | 0 | 0 | — | — | <10 | <10 | <10 |
| | | 1 | 19 | — | — | <10 | <10 | <10 |
| | | 2 | 23 | +(10) | — | 100 | <10 | <10 |
| | | 3 | 48 | +(10) | — | ND | ND | ND |
| 69 | SP-10 IIIB(C) | 0 | 0 | — | — | ND | ND | ND |
| | | 3 | 43 | +(20) | — | ND | ND | ND |
| 76 | SP-10 RF(A)-TT | 0 | 0 | — | — | ND | ND | ND |
| | | 1 | 15 | — | +(40) | ND | ND | ND |
| | | 2 | 29 | — | +(>80) | ND | ND | ND |
| | | 3 | 43 | — | +(>80) | ND | ND | ND |
| 84 | SP-22 IIIB-TT (control) | 0 | 0 | — | — | <10 | <10 | <10 |
| | | 2 | 23 | — | — | <10 | <10 | <10 |
| | | 3 | 48 | — | — | ND | ND | ND |
| 80 | TT-MBS (control) | 0 | 0 | — | — | ND | ND | ND |
| | | 2 | 21 | — | — | ND | ND | ND |

[1]Synthetic peptides were coupled to tetanus toxoid (TT) with m-maleimidobenzoyl-N-hydroxysuccinimide ester (MBS). SP-10 RF(A) = CRKSITKGPGRVIY; SP-10 IIIB(C): CTRKSIRIQRGPGRY
[2]Values in parentheses are the inverse of serum dilutions that inhibited the number of syncytia (60–80) per well by >80%.
[3]Neutralization was determined by evaluation of reverse transcriptase activity in supernatants of H-9 cells cultured for 10 days in the presence of 100 infectious units of HIV isolates. Values are inverse of anti-serum dilutions that inhibited reverse transcriptase activity by >80%.
ND = NOT DONE Therefore, the above-described ability of goat anti-SP-10 sera to inhibit HTLV-III$_B$ infectivity in the syncytium inhibition assay and in the reverse transcriptase assay, indicated that anti-SP-10 antibodies are capable TABLE V-continued SP-10-TT and SP-10-BSA DO NOT INHIBIT ANTIGEN
SPECIFIC PROLIFERATIVE RESPONSES OF NORMAL
HUMAN PERIPHERAL BLOOD LYMPHOCYTES

| Additive to Normal Human Peripheral Blood Lymphocytes in Culture | Exp. No. 1 | Exp. No. 2 |
|---|---|---|
| | CPM × 10$^6$ Lymphocytes | |
| TT (1:32) | | |

TT = Tetanus toxoid (Wyeth Laboratories, Philadelphia, Pa.), BSA = bovine serum albumin.
CPM = counts per minute of tritiated thymidine incorporation as described (Denning et al J. Immunol. 138:680, 1987).

As seen in Table V, SP-10-TT alone was as good an antigen-specific T cell activator as TT alone. Moreover SP-10-TT and SP-10-BSA when added to TT alone did not inhibit TT induced proliferation by normal T cells. In addition, anti-SP-10 goat serum did not bind to peripheral blood lymphocytes or monocytes in indirect immunofluorescence assay using flow cytofluorometry.

These data indicate that the SP-10 peptide does not perturb normal human T cell function that is dependent on a functional CD4 (T4) molecule but does induce antibodies that will inhibit HIV gp120-CD4 (T4) interactions and neutralize HIV in reverse transcriptase inhibition assays.

EXAMPLE 6

Isolate Specific Neutralization of HIV

Synthetic peptide SP-10 has an amino acid sequence derived from and unique to the gp120 envelope protein of HIV isolates HTLV-III$_B$ and LAV, while other HIV isolates have varying degrees of differing amino acid sequences in their SP-10-like gp120 envelope proteins. Synthetic peptide SP-10 (that is, SP-10-III$_B$) from the HTLV-III$_B$ isolate of HIV was coupled to tetanus toxoid and used to raise antibodies in goats (0.5 mg of conjugate per kg goat body weight) as described by Palker et al. (*Proc. Nat'l. Acad. Sci. (USA)* 84:2479, 1987). Goat antibodies raised to synthetic peptide SP-10 were tested for the ability to neutralize four different HIV isolates (FIG. 5A: HTLV-III$_B$, FIG. 5B: HTLV-III$_{RF}$, FIG. 5C: HTLV-III$_{MN}$, FIG. 5D: HTLV-III$_{SC}$). Goat anti-SP-10 antiserum ●, pre-immune goat serum (O) and AIDS patient serum (◆) all at a 1/10 dilution were first incubated with dilutions (10$^{-1}$, 10$^{-2}$, 10$^{-3}$) of each virus isolate. Next, these virus isolates were tested for the ability to infect H-9 T cells by cocultivation of virus and cells for 10 days in vitro. Levels of HIV present in cell culture supernatants after 10 days in culture were estimated by measuring RT activity in supernatants, and results are expressed as cpm values obtained in RT assay. Increased cpm values in RT assay reflect increased levels of HIV in culture.

As shown in FIG. 5A, goat anti-SP-10 antiserum inhibited (i.e. neutralized) HTLV-III$_B$ infection of H-9 cells at a virus dilution of 10$^{-2}$. Pre-immune goat serum did not inhibit HTLV-III$_B$ infection at the same dilution of virus. In contrast, goat anti-SP-10 antiserum did not neutralize other isolates of HIV (FIGS. 5 B-D). AIDS patient antibodies neutralized all four isolates of HIV (FIGS. 5 A-D). The data indicate that goat antiserum to synthetic peptide SP-10 neutralizes the HTLV-III$_B$ isolate that contains in its gp120 envelope protein the amino acid sequence present in SP-10.

EXAMPLE 7

Binding of Goat Anti-SP-10 Serum To HTLV-III$_B$- But Not To HTLV-III$_{RF}$-Infected H9 T Cells The reactivity of goat anti-SP-10 serum and autologous prebleed control serum were compared on either uninfected H9 T cells, H9 T cells infected with HIV isolate HTLV-III$_B$, or H9 T cells infected with HIV isolate HTLV-III$_{RF}$ using flow cytofluorometry and a Coulter EPICS V cytofluorograph (Haynes, *Immunol. Rev.* 57: 127, 1981; Haynes et al., *New Eng. J. Med.* 304:319, 1981).

Figure 6A:
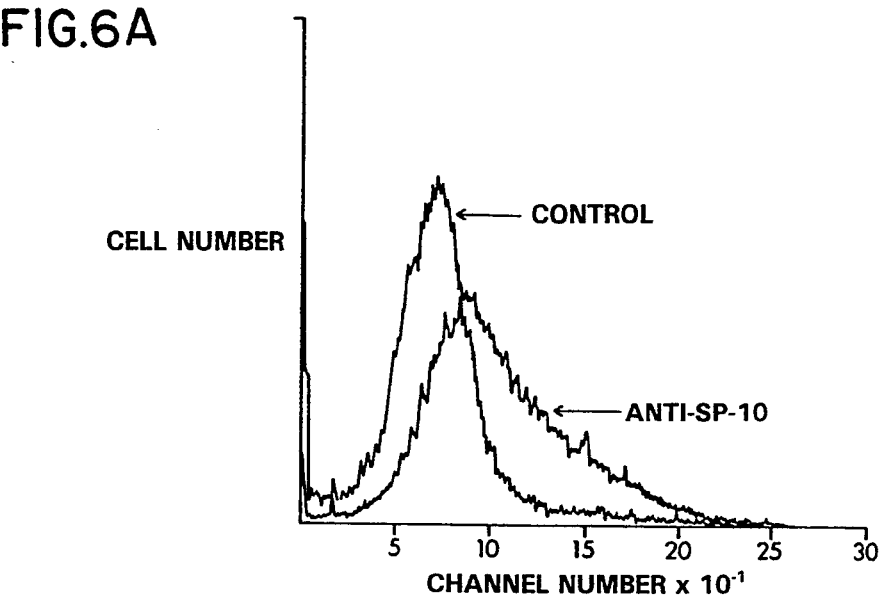
(FIG. 6A) Goat anti-SP-10 serum (1:200) reacted with 40% of HTLV-III$_B$-infected H9 T cells compared to HTLV-III$_B$-infected H9 cells incubated with control (prebleed) goat serum (FIG. 6B) Neither goat anti-SP-10 nor control (prebleed) serum (1:50) reacted with the non-infected H9 T cells.
Figure 6B:
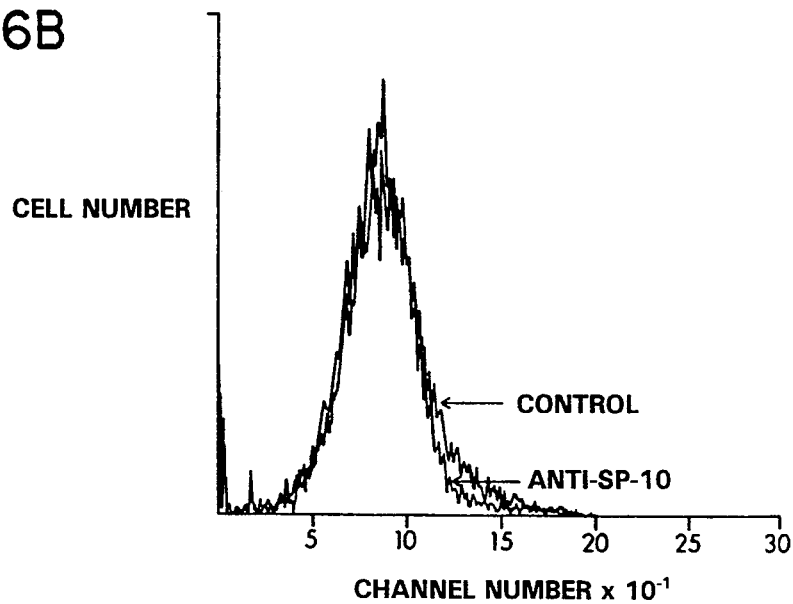
FIG. 6. Binding of goat anti-SP-10 serum to HTLV-III$_B$- but not to HTLV-III$_{RF}$-infected H9 T cells.
(FIG. 6C) Neither control (prebleed) nor anti-SP-10 serum (1:50) bound to H9 T cells infected with the HTLV-III$_{RF}$ isolate of HIV.
Figure 6C:
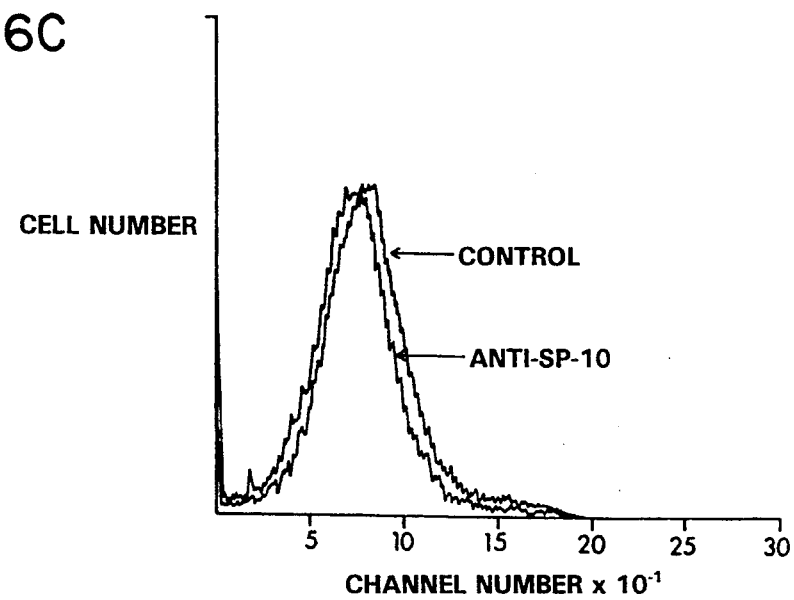

Goat anti-SP-10 serum (1:200) reacted with 40% of HTLV-III$_B$-infected H9 T cells compared to HTLV-III$_B$-infected H9 cells incubated with control (prebleed) goat serum (1:200) (FIG. 6A). Neither goat anti-SP-10 nor control (prebleed) serum (1:50) reacted with noninfected H9 T cells (FIG. 6B). Neither control (prebleed) nor anti-SP-10 serum (1:50) bound to H9 T cells infected with the HTLV-III$_{RF}$ isolate of HIV (FIG. 6C).

The foregoing invention has been described in some detail by way of examples for purposes of clarity and understanding. It will be obvious to those skilled in the art from a reading of the disclosure that the synthetic peptides of the instant invention may differ slightly in amino acid sequence from the sequences of SP-10 regions of specific HIV isolates, without departing from the scope of the invention. It will also be obvious that various combinations in forms and detail can be made without departing from the scope of the invention.

What is claimed is:

1. A method of determining the presence in mammalian serum of antibodies against a specific strain of HIV-1 comprising the steps of: (i) contacting a SP-10 peptide of said HIV-1 strain with said mammalian serum under conditions such that a complex between said peptide and said antibodies present in said mammalian serum can form; and (ii) measuring the formation of said complex.

2. A method according to claim 1 wherein said peptide is selected from the group consisting of SP-10 IIIB, SP-10 MN, SP-10 RF, SP-10 SC, SP-10 WMJ-1, SP-10 WMJ-2, SP-10 WMJ-3, SP-10 ARV-2 and SP-10-LAV-I.

* * * * *

UNITED STATES PATENT AND TRADEMARK OFFICE
CERTIFICATE OF CORRECTION

PATENT NO. : 5,352,576
DATED : October 4, 1994
INVENTOR(S) : HAYNES et al

It is certified that error appears in the above-indentified patent and that said Letters Patent is hereby corrected as shown below:

Column 1, line 10, insert the following:

--This invention was made with Government support under Grant No. CA-43447 awarded by National Institutes of Health. The Government has certain rights in the invention.--

Signed and Sealed this

First Day of October, 1996

Attest:

BRUCE LEHMAN

Attesting Officer

Commissioner of Patents and Trademarks